(12) United States Patent
Sandusky et al.

(10) Patent No.: US 8,262,594 B2
(45) Date of Patent: Sep. 11, 2012

(54) REINFORCED SUPPORT DEVICE

(75) Inventors: Donald A. Sandusky, Landenberg, PA (US); Ryan Altenburger, Landenberg, PA (US)

(73) Assignee: Warrior Sports, Inc., Warren, MI (US)

( * ) Notice: Subject to any disclaimer, the term of this patent is extended or adjusted under 35 U.S.C. 154(b) by 237 days.

(21) Appl. No.: 12/464,773

(22) Filed: May 12, 2009

(65) Prior Publication Data

US 2009/0281470 A1 Nov. 12, 2009

Related U.S. Application Data

(60) Provisional application No. 61/052,488, filed on May 12, 2008.

(51) Int. Cl.
*A61F 5/00* (2006.01)
*A61F 5/37* (2006.01)
*A41D 19/00* (2006.01)

(52) U.S. Cl. ............... 602/5; 602/21; 602/22; 128/878; 128/879; 2/159; 2/161.1

(58) Field of Classification Search .............. 602/21, 602/22, 64, 20, 5, 12; 128/878–890; 2/163, 2/161.1, 16, 20, 21, 455, 161.6, 161.5, 161.7, 2/161.2

See application file for complete search history.

(56) References Cited

U.S. PATENT DOCUMENTS

| | | | |
|---|---|---|---|
| 6,503,218 B1 | 1/2003 | Ascheman | |
| 6,557,177 B2 | 5/2003 | Hochmuth | |
| 6,923,781 B2 | 8/2005 | Gardner et al. | |
| 6,990,689 B1 | 1/2006 | Thellmann | |
| 7,234,172 B1 * | 6/2007 | Hoelscher | 2/161.1 |
| 7,293,296 B1 * | 11/2007 | Beraznik et al. | 2/161.1 |
| 7,320,145 B2 | 1/2008 | Hochmuth | |
| 8,028,347 B2 * | 10/2011 | Chang | 2/161.1 |
| 2006/0211964 A1 * | 9/2006 | Farrell et al. | 602/5 |
| 2007/0226866 A1 * | 10/2007 | Geyer et al. | 2/16 |

* cited by examiner

*Primary Examiner* — Patricia Bianco
*Assistant Examiner* — George N Phillips
(74) *Attorney, Agent, or Firm* — Warner Norcross & Judd LLP

(57) ABSTRACT

This invention relates to a reinforced support device suitable for the protection of a body part against overextension. In particular, this invention relates to a device comprising at least one reinforcement spine used to protect a body part against overextension and a plate disposed below a portion of the spine used to provide additional support and comfort. The reinforcement spine can flex in direction of the body part's natural movement and is substantially inflexible in the direction of overextension. Together, the reinforcement spine and plate prevent overextension of the protected body part and disperse the incident forces by transferring those forces from the reinforcement spine to the plate.

20 Claims, 10 Drawing Sheets

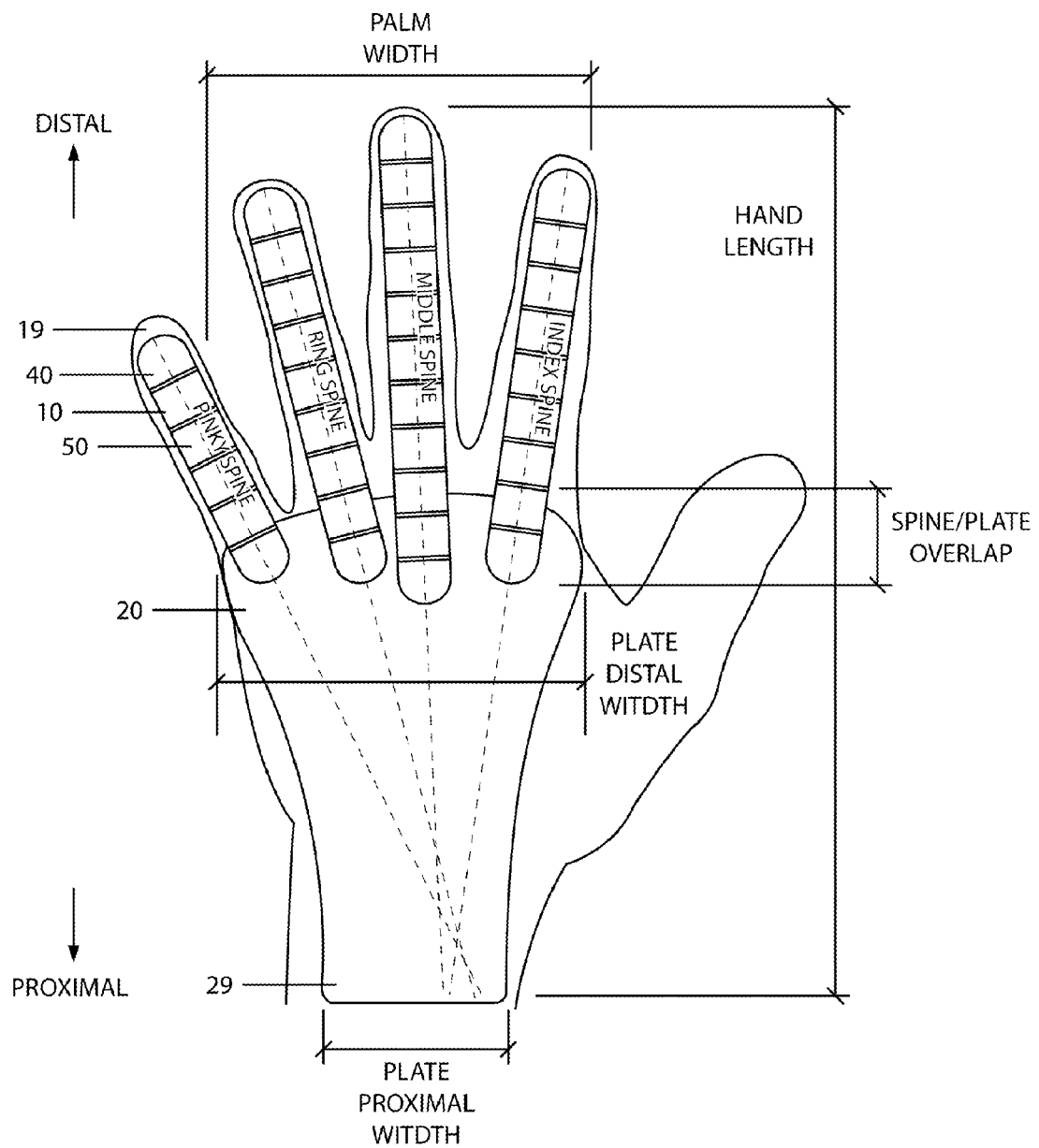

REINFORCED SUPPORT DEVICE

CROSS REFERENCE TO RELATED APPLICATIONS

This application claims the benefit of U.S. Provisional Application No. 61/052,488 filed May 12, 2008, the contents of which is incorporated herein by reference.

FIELD OF THE INVENTION

This invention relates to a reinforced support device suitable for the protection of a body part against overextension. In particular, this invention relates to a device comprising at least one reinforcement spine used to protect a body part against overextension and a plate in contact with the spine used to provide additional support and comfort by deflecting pressure. The reinforcement spine is adapted flex [the] in the direction of the body part's natural movement and is substantially inflexible in the opposite direction, i.e. overextension. Together, the reinforcement spine and plate prevent overextension of the protected body part, in part, by transferring incident forces applied to the protected body part from the reinforcement spine to the plate where the forces are dispersed.

BACKGROUND

The human body contains many body parts that are flexible, but prone to injury from overextension (e.g. hyperversion and hyperextension). One example is the fingers. Fingers can be flexed into a fist, but are prone to hyperextension if flexed in the opposite direction. Another example is the ankle. The ankle can be extended laterally, but is prone to hyperversion (e.g. sprained ankle). Hyperversion and hyperextension most often occur when a force is applied to the particular body parts such that these parts are bent beyond the typical range of motion.

With respect to fingers, hyperextension can occur while participating in many different activities. For instance, finger hyperextension may occur while participating in sports, particularly to soccer goalkeepers, baseball catchers, ice hockey goalies and snowboarding enthusiasts. It may also occur to workers participating in manual labor or industrial related jobs.

Protection against finger hyperextension has been investigated. U.S. Pat. No. 7,065,795, herein incorporated by reference in its entirety, relates to a goalkeeper glove comprising a reinforcement on the outer hand part. The reinforcement, however, comprises a single flexible piece extending over the back of the hand and fingers. This single reinforcement, being flexible, is not rigid enough to effectively disperse a force over the back of the hand. Moreover, the single unit construction, if sufficiently rigid, would simply relocate the localized force from the base of the finger reinforcement spine to the single unit's edge near the wrist rather than disperse the force over the wrist to the larger forearm, a broad area.

U.S. Pat. Nos. 6,557,177; 6,990,689 and 7,320,145, herein incorporated by reference in their entirety, relate to soccer goalkeeper gloves comprising finger reinforcements only. Typically, these reinforcements exert pressure directly onto the back of the hand when fingers are extended and do not possess a mechanism to disperse the force from the fingers over a broader area.

With respect to the ankle, the ankle joint permits two types of pivotal movement of the talus or ankle bone about the leg bone, namely a generally up and down pivotal movement of the foot within the plane of the leg bone, commonly referred to as dorsiflexion and plantarflexion, and lateral side-to-side pivotal movement of the foot relative to the ankle, commonly referred to as inversion and eversion. As is well known, excessive inversion ("hyperinversion") and excessive eversion ("hypereversion") of the foot can damage the ligaments at the ankle joint and cause ankle sprain which is a painful and sometimes debilitating injury.

Protection against ankle hyperversion has been investigated. U.S. Pat. No. 6,503,218, herein incorporated by reference in its entirety, relates to an in-the-shoe ankle brace for protecting ankle ligaments against injury resulting from hyperversion of the foot relative to the ankle. The brace comprises an ankle brace that wraps around the leg at the ankle and straps that old the brace in place. To resist hyperversion, the brace/strap design works countering the force of the hyperversion by pulling on the brace by the straps. The pulling force is concentrated on the strap rather than dispersed over a larger area.

U.S. Pat. No. 6,923,781, herein incorporated by reference in its entirety, relates to a brace for supporting the ankle or foot of a wearer including at least four splints and housing layers. The splints are L-shaped and cover portions of the leg and foot. However, the splints are rigid and do not disperse the force over a larger area than the splint itself.

There exists, however, an ongoing and unmet need to provide reinforced support devices that provide greater dispersion of applied force/pressure exerted on body parts while preventing the body pans from overextension.

SUMMARY OF THE INVENTION

The present invention relates to a device to protect a body part from overextension. In one embodiment, the device comprises (a) at least one reinforcement spine, wherein the spine comprises a distal end, a proximal end, a front side and a back side, wherein the spine can flex toward the front side and is substantially inflexible toward the back side; and (b) a plate, wherein the plate comprises a top side and a bottom side and wherein the front side one end of the spine contacts the top side of the plate. The device is able to effectively and comfortably disperse incident forces exerted on the spine by transferring these forces from the spine to the plate.

The present invention also relates to a reinforced glove suitable for the protection against finger hyperextension. In one embodiment, the glove comprises (a) a back side; (b) a palm side; (c) a hand section; (d) a plurality of finger sections connected to and extending from the hand section and each having a back side and a palm side, (e) at least one finger reinforcement spine, wherein the spine comprises a distal end and a proximal end, and wherein the spine is positioned on the back side of at least one finger section; and (f) a plate, wherein the plate comprises a top side and a bottom side and is positioned on the back side of the hand section, and wherein the front side of the proximal end of the spine contacts the plate. The glove is able to effectively and comfortably disperse incident forces exerted on a finger reinforcement spine by transferring these forces from the spine to the plate. Incident forces applied to fingertips are ultimately balanced by dispersed reaction forces exerted by the larger and stronger forearm.

One advantage of the present invention is the dispersion of an overextension force over the broad area (e.g. the leg/foot, back of the hand, the back/chest or the arm) rather than at a localized area (e.g. the base of the ankle, fingers, neck, elbow, knee or toes). By dispersing the force, the skin, soft tissue and/or bones are protected from greater impact and injury.

Another advantage of the present invention is the additional support provided to the body part to be protected by the configuration of the plate. These advantages are given by way of non-limiting example only, and additional benefits and advantages will be readily apparent to those skilled in the art in view of the description set forth herein.

BRIEF DESCRIPTION OF THE DRAWINGS

FIG. 10 is an illustration of the glove of example 1.

DETAILED DESCRIPTION OF THE INVENTION

Figure 1:
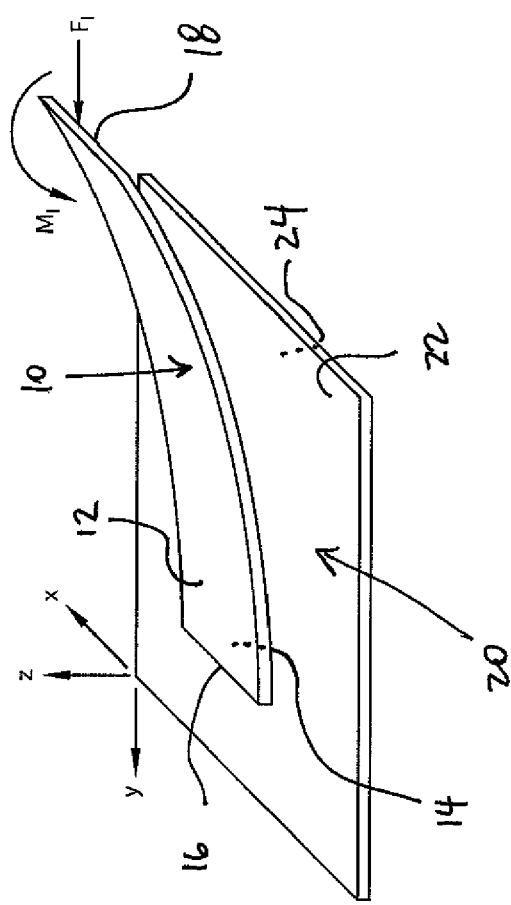
FIG. 1 is a free body diagram of the spine and the plate of the invention.

The present invention relates to a reinforced support device suitable for the protection of a body part against overextension. In particular, this invention relates to a device comprising at least one reinforcement spine positioned at a body part to be protected against overextension and a plate positioned at another body part in contact with the spine and capable of providing support and dispersing pressure. The present invention differs from conventional overextension devices by the addition of a force dispersion plate. The spine is substantially inflexible in the direction of overextension. The reinforcement spine and plate prevent overextension of a protected body part, while maintaining comfort to the user by transferring incident forces applied to the protected body part from the protected body part to the force dispersion plate.

As used herein, the term "reinforced support device suitable to protect a body part" refers to any device that provides support to a body part capable of overextension, made up of a reinforcement spine and a force dispersion plate. Some examples of the reinforcement support device incorporated into an embodiment include a glove for protecting against hyperextension of at least one finger; an ankle brace or shoe for protecting against hyperversion of the ankle; a neck brace for protecting against hyperversion of the neck; an elbow brace for protecting against hyperextension of the elbow; a knee brace for protecting against hyperextension of the knee; or a toe brace or shoe to protect against hyperextension of at least one toe. Other embodiments incorporating the reinforced support device of the invention are readily identifiable by those having skill in the art.

As used herein, the term "overextension" refers to the extension of a body part beyond the body part's normal and natural range of motion. Overextension includes hyperversion and hyperextension.

As used herein, the term "hyperextension" refers to the extension of a joint beyond the joint's normal and natural range of motion. One example is finger hyperextension, or the movement of at least one finger backwards beyond its natural range of motion that may cause injury.

As used herein, the term "hyperversion" refers to the extension of a body part having one or more joints or directions of movement beyond the body part's normal and natural range of motion. Examples include ankle hyperinversion and hypereversion, or the movement of the ankle beyond its natural range of motion that may cause injury.

As used herein, the term "reinforcement spine" refers to a flexible spine-type member that does not impair the natural movement of body parts/joints but does limit the movement of body parts/joints in a direction they are not designed to bend so as to avoid overextension.

As used herein the term "body part to be protected" refers to a body part that has a natural range of motion and may be forced beyond its natural range of motion by an external force, such as a finger, toe, ankle, arm, leg or neck.

As used herein the "body part capable of support" refers to a body part that may be in contact with the force dispersion plate.

As used herein the term "substantially inflexible" refers to the limited range of motion of the reinforced support device or reinforcement spine in the direction of overextension of a body part or joint. The degree of inflexibility will vary with the body part or joint being protected. For example, an ankle cannot be overextended beyond the normal or straight position more than a few degrees before injury may occur. In contrast, a finger may be hyperextended beyond the normal or straight position many degrees before injury may occur.

In one embodiment, the present invention is directed to a device to protect a body part from overextension, comprising (a) at least one reinforcement spine comprising a distal end, a proximal end, a front side and a back side, wherein the spine can flex toward the front side and is substantially inflexible toward the back side; and (b) a plate comprising a top side and a bottom side, wherein the front side of the proximal end of the spine contacts the plate, whereby an incident force exerted on the front side of the spine is transferred to the plate.

The reinforcement spines and plate design of the present invention provides improved protection and comfort to the user. As depicted in FIG. 1, an incident force that contacts the reinforcement spine (10) in the direction of overextension ($F_I$) is transferred to a force dispersion plate (20) having a larger area than the unrestrained end (16) of the spine (10) that contacts the plate (20). In the prior art, as the incident force ($F_I$) is applied to the reinforcement spine, the point load of the transferred force from the proximal end of the spine would be concentrated on one small area of the body supporting the body part to be protected. By employing the force dispersing plate of the present invention, the transferred force is diffused over a larger area of the body as a dispersed force.

The reinforcement spine (10) preferably has non-isotropic mechanical properties, whereas the dispersion plate (20) preferably has isotropic mechanical properties. Further, there is preferably a low friction coefficient between the spine (10) and plate (20) so that in the range of use, the two are essentially free to move in relation to one another. When the unrestrained end (16) of the spine (10) slides along the upper surface (22) of plate (20), the other end (18) of the spine (10) moves away from the incident force ($F_I$) and the incident moment ($M_I$), thereby reducing their intensity.

Figure 5:
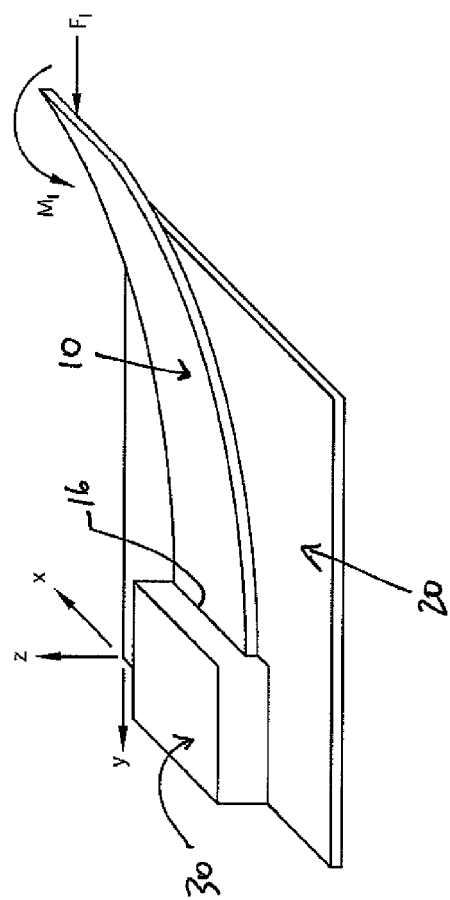
FIG. 5 is a free body diagram depicting the device of the invention incorporating a spine block.

Because the spine (10) is substantially free to slide against the upper surface (22) of the plate (20) in the y-direction until the spine (10) freely stops or until it reaches a spine block (30) (see FIG. 5), any substantial reactionary forces ($F_{RY}$ and $F_{RZ}$) in the y-direction cannot be supported, whether caused by incident moment ($M_I$) or by incident force ($F_I$) applied to the other end (18) of the spine (10). In the range of use, when the spine (10) reaches the spine block (30) or otherwise the end of its movement, the incident moment ($M_I$) has been reduced significantly. The remaining component reactionary force ($F_{RY}$ and $F_{RZ}$) is translated to the reinforcement plate (20) so that the component reactionary force in the y-direction ($F_{RY}$) is minimized and the component reactionary force in the z-direction ($F_{RZ}$) is distributed over a large area, thereby providing for comfortable dispersion the remaining incident force ($F_I$).

The purpose of the spine block is to limit the maximum distance the reinforcing spines can travel before the mechanism become effectively pinned at both ends. This is to limit extension within a comfortable range.

Figure 2:
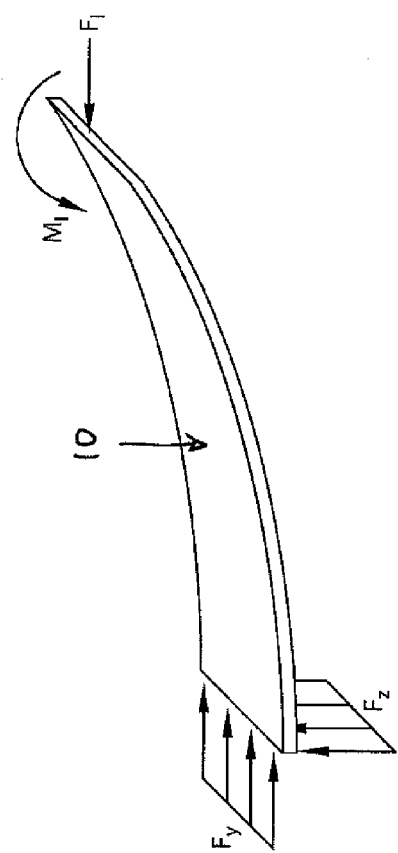
FIG. 2 is free body diagram of the resultant component forces upon application of the incident force to the spine.
Figure 3:
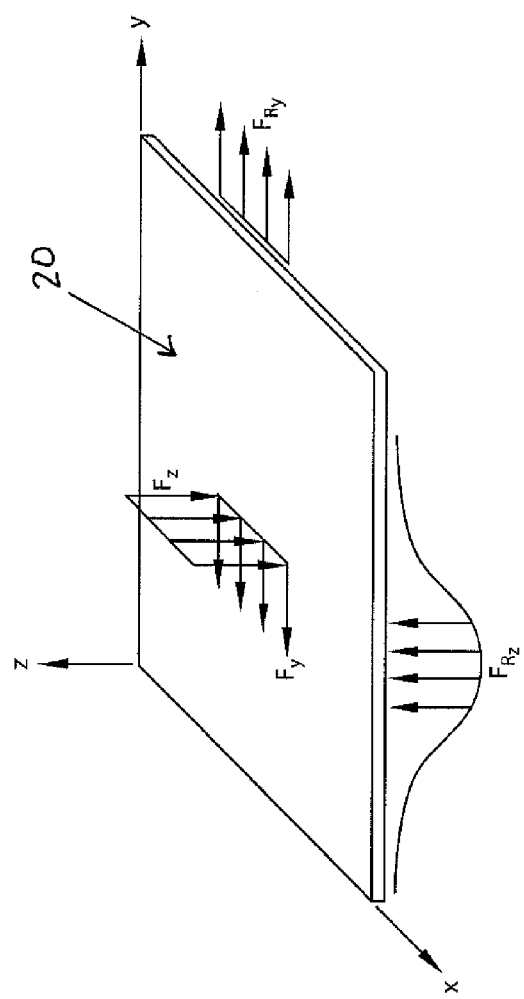
FIG. 3 is a free body diagram of the resultant reactionary forces upon application of the incident force to the spine.
Figure 4:
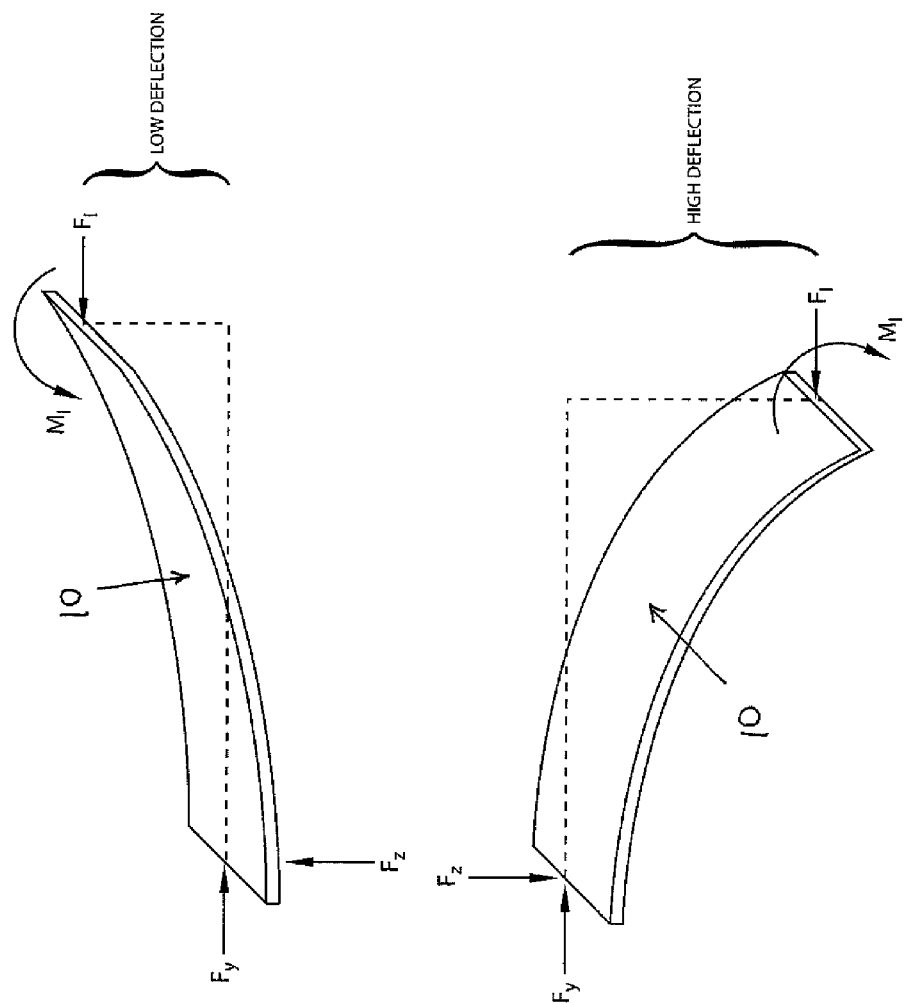
FIG. 4 is a free body diagram showing the deflection in directions of the non-isotropic spine.

FIGS. 2 and 3 depict the component and reactionary forces as they apply to this invention. FIG. 2 depicts the component forces, i.e. those forces occurring within the reinforced support device of the present invention. As depicted in FIG. 2, as the incident force ($F_I$) is applied to the body part in the direction of overextension ($F_I$), component forces ($F_y$ and $F_z$) will result at the unrestrained end (16) of the spine (10) that is in contact with the plate (20). The use of the reinforcement plate (20) results in the component force ($F_y$ and $F_z$) being distributed over a large area because the plate has isotropic mechanical properties. In other words, the point load of pressure is naturally distributed over a larger area, resulting in more comfort for the user at the point of contact.

FIG. 3 depicts the reactionary forces, i.e. the forces applied by the body part against the device, and in particular, bottom surface (24) of the plate (20), that is between the incident force ($F_I$) and the body part. Reaction forces will be distributed in the z-direction ($F_{RY}$) and the y-direction ($F_{RZ}$).

Figure 6:
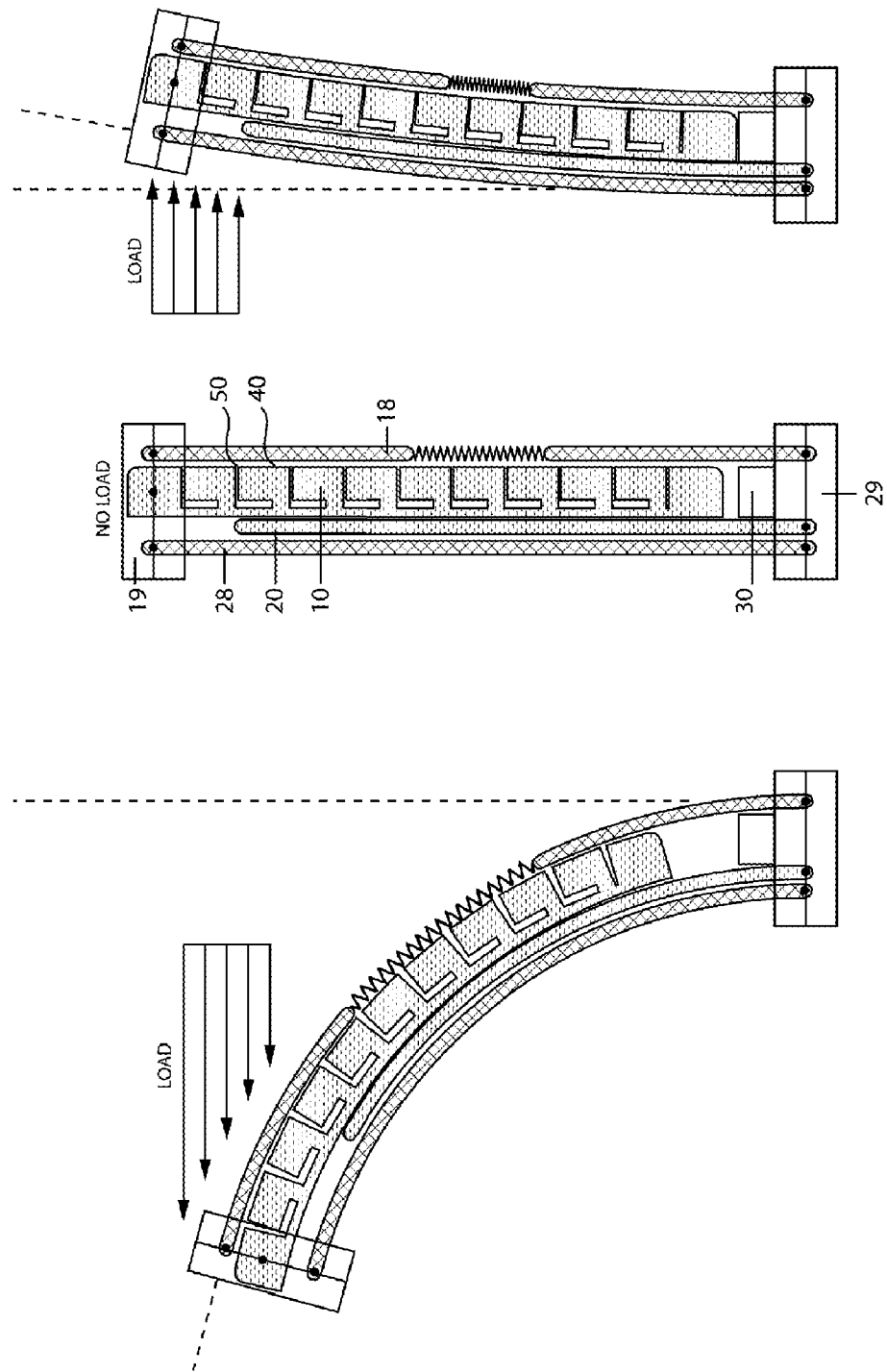
FIG. 6 is an illustration of the device of the invention.

FIG. 6 shows one preferred embodiment of reinforced support device. The device in this figure includes a reinforcement spine (10), a force dispersion plate (20), a plate covering (28), a spine covering (18), a plate connector (29), a spine connector (19), and a spine block (30). The area moment of inertia (IA), i.e. the geometry of a beam subject to deflection by bending, is one way of understanding how the support device of the present invention function. In general, a beam with higher IA will deflects less than a beam of lower IA when subjected to equivalent bending loads. As applied to the current invention, when the reinforced support device is subjected to a load in the normal flexible direction of the body part (to the left in FIG. 6), the IA is lower than when subjected to the same load in the overextension direction (to the right in FIG. 6). For example, if the height of the spine cross section, is four times greater in the overextension direction, the area moment of inertia would be sixty-four times greater calculated as by:

$$I_A = bh^3/12 \text{ (in natural direction)}$$

$$I_A = 64 \times bh^3/12 \text{ (in overextension direction)}$$

The spine connector (19) effectively pins one end of the reinforced spine to a fixed location opposite to the plate connector (29) which does the same for the plate. The spine covering (18) preferably incorporates at least a section of elastomeric material (17) that can preferably elongate 100% and recover (e.g. Spandex® knit fabric).

The reinforcement spine may be any known reinforcement, support or stiffening element known for use in medical, sport or general protection equipment industries that allows flexibility in one direction and limits flexibility in at least one other direction. For example, the reinforcement spine may be similar to the finger supports of U.S. Pat. No. 6,557,177 and U.S. Pat. No. 7,320,145.

As shown in FIG. 6, the spine may comprise segments and reliefs. The segments (40) represent one means of imparting to the spine the ability to freely flex in the direction of the body part or joint's natural range of motion and the ability to be substantially inflexible in the direction of overextension. The spine may further comprise multiple reliefs (40) that may be positioned in one or more positions between the segments (50). The purpose of the reliefs is to allow the effective height of the spine cross section to be smaller one direction and substantially larger in another so that the I.sub.A is much higher in the overextension direction than the natural direction.

The reinforcement spine may be made using any known material used to make any reinforcement, support or stiffening element known for use in medical, sport or general protection equipment industries. Preferably, these materials include plastics, polymers, rubber, metals, alloys and composites. Suitable reinforcement spine materials which may be used in the present invention have been disclosed in U.S. Pat. Nos. 6,557,177; 6,990,689 and 7,320,145. In an alternative embodiment, the relief (50) may be replaced with an elastomeric resin or rubber material.

The force dispersion plate is preferably substantially stiff and may be made using any known material used to make any plates for use in medical, sport or general protection equipment industries. Preferably, these materials may include plastics, polymers, rubber, metals, alloys and composites. The plate should have sufficient qualities, such as thickness, tensile strength, flexibility, rigidity, toughness, hardness and/or elasticity, such that the plate is able to disperse an impact, force and/or lever load from a reinforcement or support spine over a broad area. The plate should also be sized to fit snugly over the body part capable of support, and provide a large enough surface to accommodate the distance covered by the proximal end of the spine as it slides along the surface of the plate.

Dimensions of a reinforcement spine will vary substantially depending on the body part to be protected. In the case of a glove, dimensions length can range in 5-20 cm and width 1-3 cm.

Dimensions of a plate will also vary substantially depending on the body part to be protected.

The overlap of the reinforcement spine on to the plate will also vary depending on the body part, but should overlap enough that it does not come off the plate during use. See examples 2 and 3 for examples of dimensions. The dimensions of the spine(s) and plate will vary significantly depending on the body part to be protected and the size of the user.

A reinforced support device may comprise one reinforcement spine and a plate or it may comprise a plurality of reinforcement spines and a plate. The number of reinforcement spines will vary with the body part to be protected, the dimensions of the spine(s)/plate, and the amount of protection desired. For example, a reinforce support glove may comprise 1 to 5 reinforcement spines, corresponding to one or more fingers and the thumb. In contrast an ankle support may comprise 1 to 100 or more spines.

The reinforcement support device of the invention can be applied in a variety of end uses to protect various body parts, including fingers, toes, ankle, knee, elbow, neck, shoulder and back.

Gloves

In one particular application, the present invention relates to a reinforced glove suitable for the protection against finger hyperextension. The present invention differs from conventional finger hyperextension protective gloves by the addition of a force dispersion plate. Conventional gloves have finger supports to protect the fingers from hyperextension, but do not have a plate to effectively disperse a force exerted by the finger supports onto the back of the hand over a broad area. When backward pressure is applied to the fingers, such as when blocking or catching a soccer ball or being involved in an industrial accident, a lever effect load is created. At the proximal end of this lever, the finger reinforcement spines impact into the back of the hand. This impact may damage the skin and soft tissue, as well as, place intense bending loads on the small bones in the hand. The small bones in the back of the hand may be broken as they are not designed to withstand such a load.

In a preferred embodiment the present invention is a finger reinforcement system that transfers this backward pressure on the fingers to a force dispersion plate located on the back of the hand and over the larger bones of the forearm and wrist, where the pressure can be absorbed more comfortably. The design of the present invention allows the plate to distribute the load over a much broader area over the back of the hand and wrist. With the lever load transferred away from the smaller delicate bones of the hand to the larger, stronger bones of the forearm and wrist area, lesser impacts and/or less bodily injury are experienced.

In one embodiment, the present invention involves a glove suitable to protect at least one finger from hyperextension when contacted with a force, the glove comprising (a) a back side; (b) a palm side; (c) a hand section; (d) a plurality of finger sections connected to and extending from the hand section each having a back side and a palm side; (e) at least one finger reinforcement spine, wherein the spine comprises a distal end, a proximal end, a front side and a back side, wherein the spine is positioned on the back side of the finger section, and wherein the spine can flex toward the front side and is substantially inflexible toward the back side; and (f) a plate, wherein the plate is positioned on the back side of the hand section, and wherein the proximal end, front side of the finger spine contacts the plate such that a force is exerted on the front side of the spine is transferred to the plate.

A normal finger can flex a certain amount in the backwards direction without risk of overextension. Preferably, the degree of flexibility of a finger support device or finger reinforcement spine is less than that resulting in overextension or hyperextension.

The glove may comprise from 1-5 or more individual reinforcement spines.

The finger reinforcement spines are preferably flexible toward the palm side of the hand. More preferably, the spines are flexible to allow the fingers to function with no substantial impedance in the ability to flex toward the palm side of the hand. The finger reinforcement spines are also preferably partially or substantially inflexible toward the back of the hand to prevent hyperextension. More preferably, the spines may be inflexible to prevent the fingers from hyperextending beyond the normal range of anatomical movement.

The finger reinforcement spines are preferably positioned on the back side of the finger section of a glove. The glove of the present invention preferably has an interior side and an exterior side. The phrase "on the back side" includes wherein the spines are placed within or attached to the interior of the glove, on the inside of the housing material of the glove or on the exterior of the glove. The spines may be temporarily housed within the glove, or may be directly attached on, in or to the glove in any manner known in the art, such as by sewing, fastening, gluing, melting or cementing.

The force dispersion plate is preferably positioned on the back side of the palm section. The phrase "on the back side" includes wherein the plate is attached on the interior of the glove, on the inside the housing material of the glove and on the exterior of the glove. The plate may be attached on, in or to the glove in any manner known in the art, such as by sewing, fastening, gluing, melting or cementing.

Figure 7:
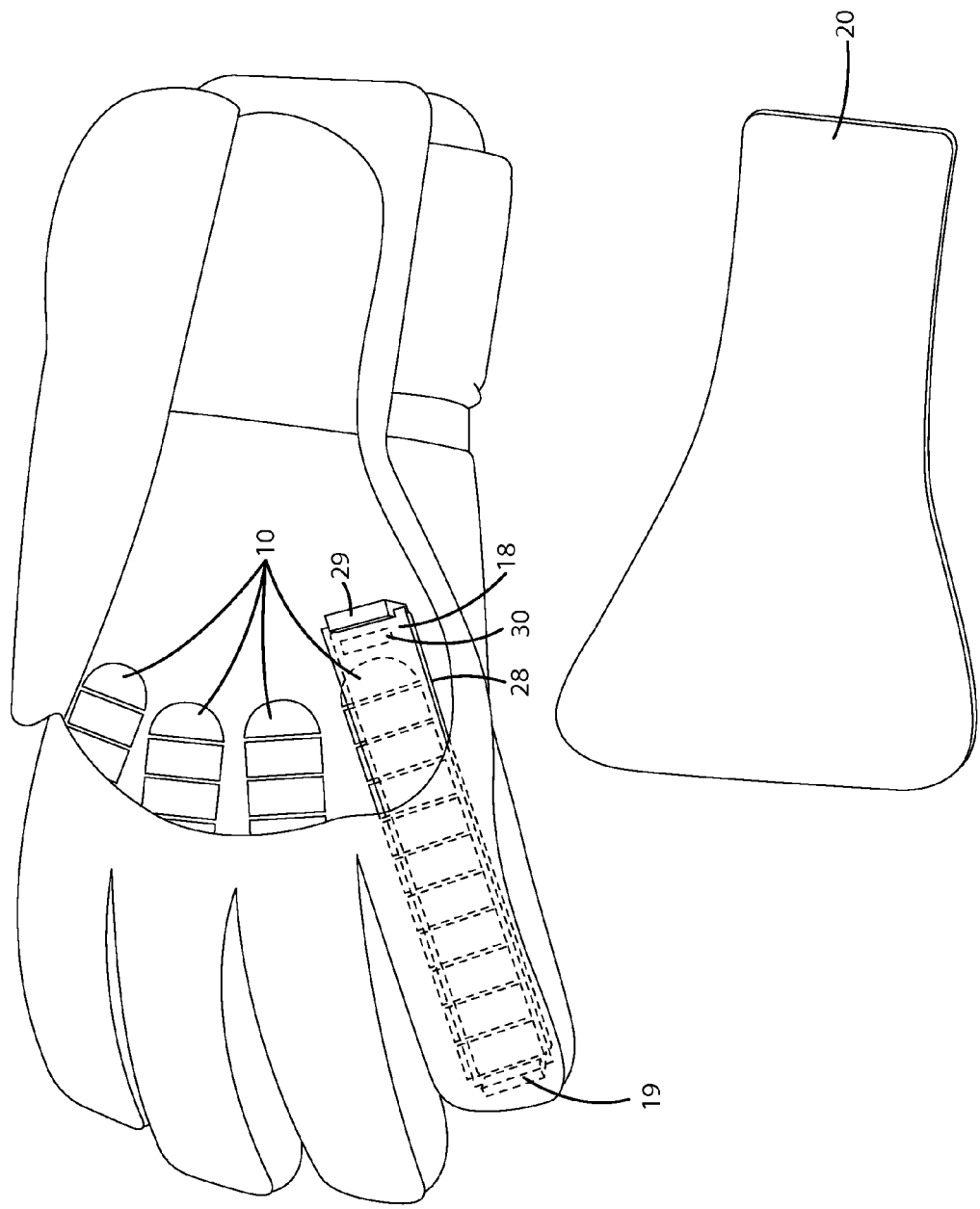
FIG. 7 is a photograph of an embodiment of the invention in the form of a glove with the plate removed.

The plate preferably covers the back of the hand where the proximal ends of the spine(s) contact the plate. Preferably, the plate substantially covers the back of the hand and extends over the entire wrist area and over a portion of the radius and ulna. FIG. 7 shows one embodiment of the plate (20). In this embodiment, the plate (20) is broad over the top of the palm and tapers to become narrow over the wrist and a portion of the radius and ulna. Plate (20) is removed from the glove in this figure.

Figure 8:
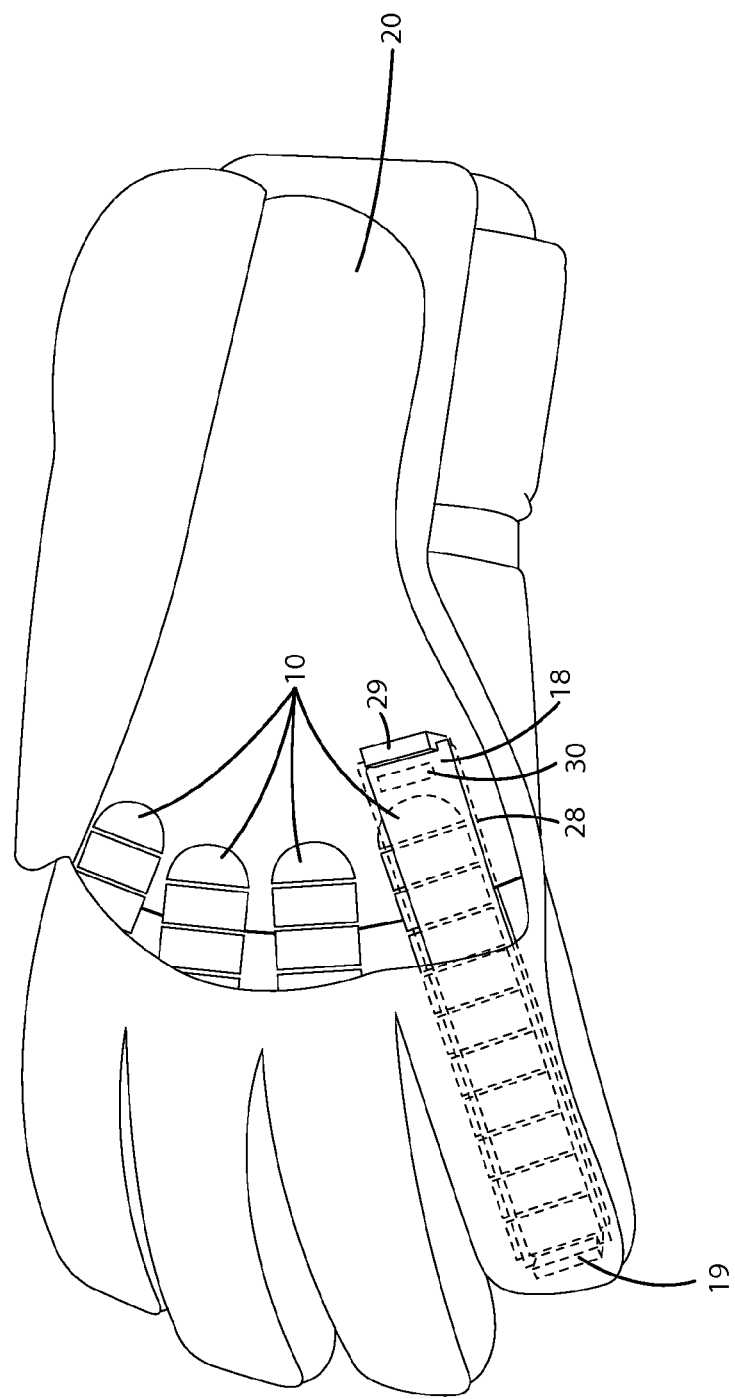
FIG. 8 is a photograph of an embodiment of the invention in the form of a glove with the plate inserted.

The finger reinforcement spines and the plate are preferably positioned such that when an incident force is placed on the fingers in the overextension direction, the force is substantially transferred to the plate. FIG. 8 shows one example of how the proximal end of the spines (10) overlap the plate (20). Preferably, the spines and the plate are in direct contact when the incident force is applied. The spines and the plate may or may not be in contact at rest when no incident force is being exerted on the fingers.

The glove of the present invention may be used as a sport glove or a work glove. In particular, the glove of the present invention may be used as a soccer goalkeeper glove, a lacrosse glove, a football glove, a baseball glove, a golf glove, a hockey glove, a ski glove, a motorcycle glove, an extreme sports glove, and a weight lifting glove. The glove of the present invention may also be used to protect the hands of persons performing manual labor and industrial related jobs.

The material used to make the housing of the glove may be any material known in the industry suitable for the manufacture of sport or work gloves. These materials may include natural materials, synthetic materials and mixtures thereof. The materials may be selected from the group consisting of cotton, leather, suede and nylon.

One skilled in the art will recognize that numerous variations or changes may be made to the glove described above without departing from the scope of the present invention. Accordingly, the foregoing description of preferred embodiments and following examples are intended to describe the invention in an exemplary, rather than a limiting, sense.

Ankle

In another particular application, the present invention relates to a reinforced ankle support or shoe for the protection against ankle overextension.

A normal ankle can flex a certain amount from side to side without risk of overextension. Preferably, the degree of flexibility of an ankle support device or an ankle reinforcement spine is less than that resulting in the overextension or hyperversion.

Figure 9:
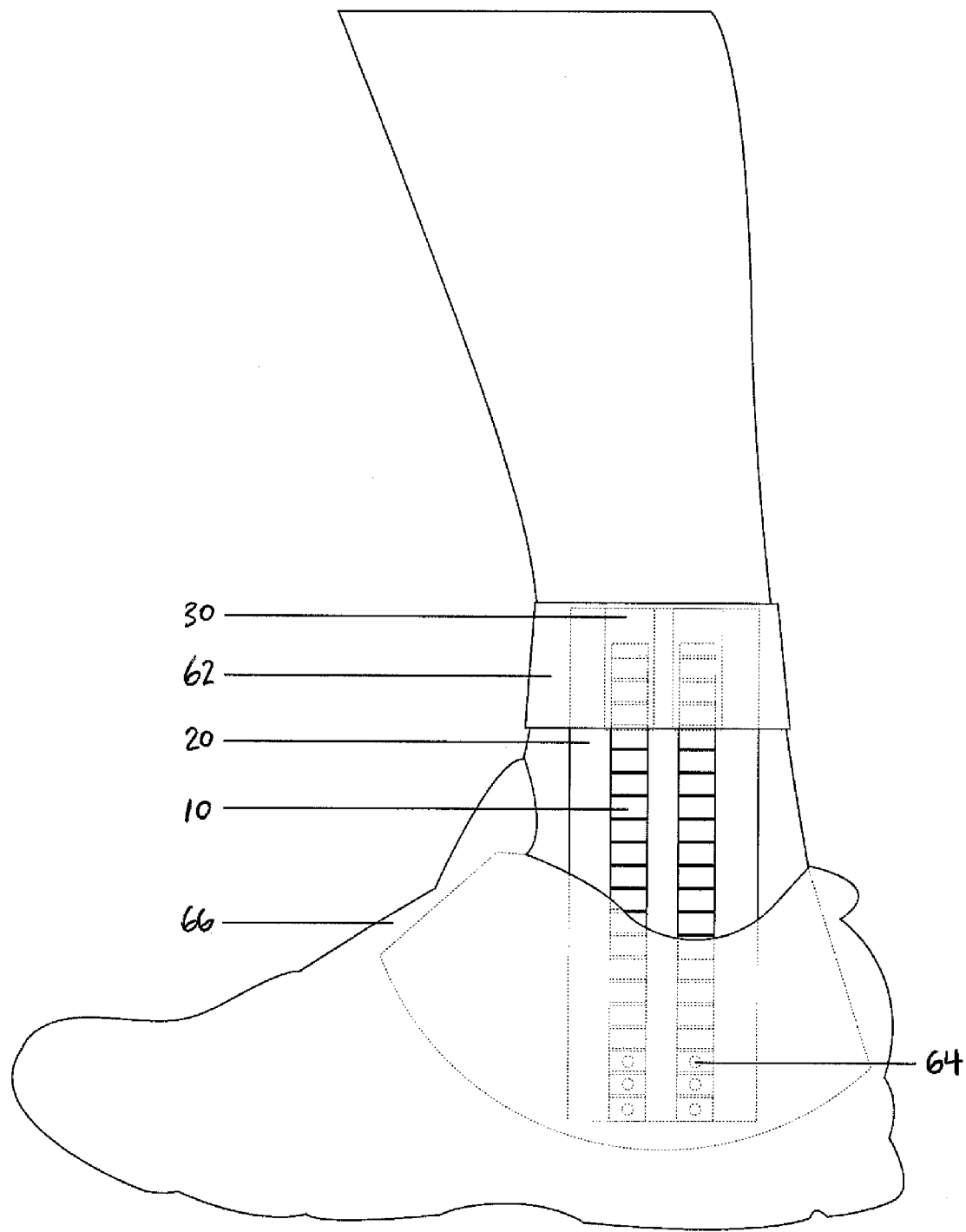
FIG. 9 is a photograph of an embodiment of the invention in the form of an ankle support.

Depicted in FIG. 9 is one embodiment of the invention when used for ankle protection. Provided in this embodiment are a plate (20) and two reinforcement spines (10). The proximal ends of both the plate and the spines are disposed above the ankle and held to the leg via an ankle strap (62) at a position on the leg above the ankle and onto the tibia and fibula such that adequate support is provided. Also provided on the plate near the proximal end of the spines (10) is a spine block (30). The distal ends of both the plate and the spines are located below the ankle. The distal ends of the spines (10) are preferably adhered (64) to the plate as shown in the Figure. Also shown in this embodiment is a plate/spine covering (66) which is preferably a lining and outside fabric.

Applicants specifically incorporate the entire content of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

EXAMPLES

Example 1

A soccer goalkeeper glove has been manufactured comprising the present invention. The reinforced goalkeeper glove is designed to allow substantially unrestricted hand movement from a clenched fist to a open, flat hand FIG. 10 illustrates, as one embodiment of the present invention a reinforced glove having finger reinforcement spines and a plate with the spine covering removed. The finger reinforcement spines are made of tough polyethylene plastic and are attached to the spine covering and plate covering at the distal tip forming the spine connector. The finger reinforcement spines are designed to be flexible primarily toward the palm sides of the hand to allow the goalkeepers finger tips to clench and grasp the ball. The proximal end of the spine is not attached to anything so it is free to slide over the distal end of the plate surface. The spine is bound only at its distal end but is encompassed between the plate and one side of the spine covering on the other side. The plate is made of tough polyethylene plastic and is attached to the plate covering and to the spine covering at the proximal end forming the plate connector. The plate covers a majority of the back of the hand and extends over the entire wrist area to the distal end of the radius and ulna bones of the forearm. The finger reinforcement spines overlap the plate to allow incident forces and/or incident movement loads to be spread out and to be resisted by disperse reactionary forces applied by the stronger forearm area. FIG. 10 shows a reinforced glove wherein the plate has been removed. The finger reinforcement spines are present in the back of the forefinger section.

Example 2

Using the soccer glove of Example 1, the below table sets forth the dimensions and positioning of a small sized glove.

TABLE 2

| Size 6 Carplgard ™ Glove | | | |
|---|---|---|---|
| | Spine Length (CM) | Spine Width (CM) | Spine/Plate Overlap Length (CM) |
| Index Spine | 11.0 | 2.0 | 2.5 |
| Middle Spine | 13.0 | 2.0 | 4.0 |
| Ring Spine | 10.0 | 2.0 | 2.0 |
| Pinky Spine | 8.0 | 2.0 | 1.5 |
| Plate Length | 14.0 | | |
| Plate Distal Width | 8.5 | | |
| Plate Proximal Width | 4.0 | | |
| Index Space Length | 23.0 | | |
| Middle Space Length | 24.0 | | |
| Ring Space Length | 23.0 | | |
| Pinky Space Length | 21.0 | | |
| Plate Thickness | 2.0 | | |
| Plate Pad Thickness | 2.0 | | |

TABLE 2-continued

| Size 6 Carplgard ™ Glove | | | |
|---|---|---|---|
| | Spine Length (CM) | Spine Width (CM) | Spine/Plate Overlap Length (CM) |
| Palm Width | 11.0 | | |
| Glove Length | 24.5 | | |

Example 3

Using the soccer glove of Example 1, the below table sets forth the dimensions and positioning of a larger sized glove.

TABLE 3

| Size 10 Carplgard ™ Glove | | | |
|---|---|---|---|
| | Spine Length (CM) | Spine Width (CM) | Spine/Plate Overlap Length (CM) |
| Index Spine | 14.6 | 2.0 | 4.5 |
| Middle Spine | 16.6 | 2.0 | 4.0 |
| Ring Spine | 13.5 | 2.0 | 2.0 |
| Pinky Spine | 10.0 | 2.0 | 1.5 |
| Plate Length | 17.0 | | |
| Plate Distal Width | 10.0 | | |
| Plate Proximal Width | 5.0 | | |
| Index Space Length | 28.0 | | |
| Middle Space Length | 29.0 | | |
| Ring Space Length | 28.0 | | |
| Pinky Space Length | 25.0 | | |
| Plate Thickness | 2.0 | | |
| Plate Pad Thickness | 2.0 | | |
| Palm Width | 14.0 | | |
| Glove Length | 29.0 | | |

What is claimed is:

1. A device to protect a body part from overextension, comprising:
    at least one reinforcement spine comprising a first end, a second end, a front side and a back side, wherein the at least one reinforcement spine can flex forwardly toward the front side in response to a bending load free of substantial resistance, wherein the at least one reinforcement spine does not impair a flexing of the body part forwardly, the at least one reinforcement spine being substantially inflexible rearwardly toward the back side, substantially beyond an unflexed position, to oppose an overextension force; and
    a plate comprising an upper surface and a lower surface, wherein the front side of the second end of the at least one reinforcement spine slidably engages the upper surface of the plate, whereby the overextension force exerted on the at least one reinforcement spine is transferred to the plate,
    wherein the front side of the second end of the at least one reinforcement spine slides along a path relative to the upper surface of the plate when the overextension force exerted on the at least one reinforcement spine is transferred to the plate.

2. The device of claim 1, further comprising a spine block, the spine block being positioned adjacent the second end of the at least one reinforcement spine, wherein the spine block is located within the path and adapted to limit the sliding of the at least one reinforcement spine relative to the upper surface of the plate.

3. The device of claim 1 wherein the plate is secured to a plate connector.

4. The device of claim 1 comprising a front covering, wherein the front covering is fixedly and immovably secured directly to the first end, wherein the front covering is further fixedly and immovably secured to the plate at a first location distal from the first end.

5. The device of claim 1 wherein the at least one reinforcement spine is secured to a spine connector.

6. The device of claim 5 wherein the plate is secured to a plate connector, wherein the spine connector pins the first end of the at least one reinforcement spine to a fixed location opposite the plate connector.

7. The device of claim 1 comprising a covering, wherein the covering is fixedly joined directly to the first end of the at least one reinforcement spine so that as a body part is flexed to a flexed mode, the first end of the at least one reinforcement spine moves away from the plate.

8. The device of claim 7 wherein the plate includes a plate distal end that is located distal from the at least one reinforcement spine, wherein the covering is fixedly joined directly to the plate distal end opposite the first end of the at least one reinforcement spine so that as a body part is flexed to a flexed mode, the plate distal end remains substantially stationary relative to the body part, and the second end of the at least one reinforcement spine slides along the upper surface of the plate away from the plate distal end.

9. A glove suitable to protect a finger from hyperextension when contacted with a force, the glove comprising:
  a back side;
  a palm side;
  a hand section;
  a plurality of finger sections connected to and extending from the hand section and each having a back side and a palm side;
  at least one finger reinforcement spine, wherein the at least one finger reinforcement spine comprises a distal end, a proximal end, a front side, and a segmented back side defining a plurality of spaced apart lateral reliefs, wherein the at least one finger reinforcement spine is positioned on the back side of the finger section, and wherein the at least one finger reinforcement spine can freely flex in response to a bending load toward the front side and can oppose a bending load toward the back side;
  a plate, wherein the plate is positioned on the back side of the hand section, and wherein the proximal end, front side of the at least one finger reinforcement spine slidably engages the plate such that a rearward bending load exerted on the at least one finger reinforcement spine is transferred to the plate; and
  a spine block adjacent the proximal end of the at least one reinforcement spine, the at least one reinforcement spine being moveable apart from the spine block in response to a forward bending load to define a gap therebetween,
  wherein the front side of the proximal end of the at least one finger reinforcement spine slides relative to the upper surface of the plate and toward the spine block when the rearward bending load is transferred to the plate, wherein the spine block opposes further sliding of the at least one reinforcement spine relative to the upper surface of the plate.

10. The glove of claim 9 wherein the distal end of the at least one finger reinforcement spine is secured to the glove.

11. The glove of claim 9 comprising a spine connector, and a covering having a distal covering end, the spine connector fixedly and immovably joining the distal covering end with the distal end of the at least one finger reinforcement spine so that when a finger flexes, the distal covering end pulls the distal end of the at least one finger reinforcement spine away from the plate with the proximal sliding along the upper surface of the plate.

12. The glove of claim 9 wherein the glove further comprises a wrist section and the plate is positioned over the wrist section.

13. The glove of claim 9 wherein the plate is fixedly secured to the glove with a plate connector, wherein the distal end of the at least one finger reinforcement spine is fixedly secured to the glove with a spine connector, wherein the plate connector and spine connector are distal from one another.

14. The glove of claim 13 wherein the distal end of the at least one finger reinforcement spine is secured to the glove.

15. The device of claim 9 comprising:
  a covering adjacent the at least one finger reinforcement spine;
  a spine connector; and
  a plate connector distal from the spine connector,
  wherein the spine connector fixedly and immovably secures the distal end of the at least one finger reinforcement spine to a fixed location relative to the covering opposite the plate connector.

16. The device of claim 15 wherein the plate connector fixedly secures the plate to the covering.

17. The device of claim 15 wherein the spine connector fixedly secures the distal end of the at least one finger reinforcement spine to the covering, but not to the plate.

18. The device of claim 15 wherein the plate connector secures the plate to the covering, but not to the at least one finger reinforcement spine.

19. A device to protect a body part from overextension comprising:
  at least one reinforcement spine comprising a first end, a second end, a front side and a back side, wherein the at least one reinforcement spine can flex toward the front side and is substantially inflexible toward the back side;
  a plate comprising an upper surface and a lower surface, wherein the front side of the second end of the at least one reinforcement spine slidably engages the upper surface of the plate, whereby a force exerted on the front side of the at least one reinforcement spine is transferred to the plate, wherein the front side of the second end of the at least one reinforcement spine slides along a path relative to the upper surface of the plate when the force is transferred to the plate;
  a front covering, wherein the front covering is fixedly and immovably secured directly to the first end, wherein the front covering is further fixedly and immovably secured to the plate at a first location distal from the first end; and
  a back covering, wherein the back covering is fixedly and immovably secured directly to the first end, wherein the back covering is also fixedly and immovably secured to the plate at a second location distal from the first end.

20. The device of claim 19 wherein the first location and second location are adjacent one another, wherein stitching joins the front covering and the back covering at the first location.

* * * * *